US009572608B2

(12) United States Patent
Hansell et al.

(10) Patent No.: US 9,572,608 B2
(45) Date of Patent: *Feb. 21, 2017

(54) LOCKING CONFIRMATION MECHANISM FOR A BONE SCREW AND PLATE ASSEMBLY

(71) Applicant: Globus Medical, Inc., King of Prussia, PA (US)

(72) Inventors: Noah Hansell, King of Prussia, PA (US); Michael Black, Spring City, PA (US)

(73) Assignee: Globus Medical, Inc., Audubon, PA (US)

( * ) Notice: Subject to any disclaimer, the term of this patent is extended or adjusted under 35 U.S.C. 154(b) by 44 days.

This patent is subject to a terminal disclaimer.

(21) Appl. No.: 14/060,830

(22) Filed: Oct. 23, 2013

(65) Prior Publication Data

US 2014/0046377 A1 Feb. 13, 2014

Related U.S. Application Data

(63) Continuation of application No. 13/186,187, filed on Jul. 19, 2011, now Pat. No. 8,591,556.

(51) Int. Cl.
*A61B 17/80* (2006.01)
*A61B 17/86* (2006.01)
*A61B 17/88* (2006.01)

(52) U.S. Cl.
CPC ....... *A61B 17/8033* (2013.01); *A61B 17/8042* (2013.01); *A61B 17/8047* (2013.01); *A61B 17/8052* (2013.01); *A61B 17/88* (2013.01)

(58) Field of Classification Search
CPC . A61B 17/80; A61B 17/8033; A61B 17/8042; A61B 17/8047; A61B 17/86; A61B 17/8665; A61B 17/8685; A61B 17/8695; A61B 2017/867
USPC .................................... 606/280–299; 411/14
See application file for complete search history.

(56) References Cited

U.S. PATENT DOCUMENTS

| 5,876,402 | A | 3/1999 | Errico et al. |
| 6,258,089 | B1 | 7/2001 | Campbell et al. |
| 7,662,154 | B2 | 2/2010 | Ribeiro |
| 7,727,266 | B2 | 6/2010 | Lindemann et al. |
| 2006/0122604 | A1 | 6/2006 | Gorhan et al. |
| 2007/0123884 | A1* | 5/2007 | Abdou ........................... 606/69 |
| 2008/0097442 | A1 | 4/2008 | Dixon |

(Continued)

OTHER PUBLICATIONS

Synthes, "Dual Core and Double Lead. Synthes pedicle screw design." 2007.*

*Primary Examiner* — Kevin T Truong
*Assistant Examiner* — Tracy Kamikawa

(57) ABSTRACT

Novel bone screw and plate assemblies including locking confirmation mechanisms are provided. In certain cases, a locking confirmation mechanism is operably attached to the plate, and comprises a toggling arm having an upper portion, a mid-portion and a lower portion. When a bone screw is positioned in a plate in an unlocked configuration, the locking confirmation mechanism assumes a first position. When the bone screw is positioned in the plate in a locked configuration, this causes the locking confirmation mechanism to pivot and assume a second position. The locking confirmation mechanism thus provides a convenient visual and/or tactile means to assess when the screw is in a locked configuration.

18 Claims, 3 Drawing Sheets

(56) References Cited

U.S. PATENT DOCUMENTS

2009/0024170 A1* 1/2009 Kirschman ........ A61B 17/8052
 606/280
2009/0131988 A1 5/2009 Bush, Jr. et al.
2010/0256686 A1 10/2010 Fisher et al.

* cited by examiner

LOCKING CONFIRMATION MECHANISM FOR A BONE SCREW AND PLATE ASSEMBLY

CROSS-REFERENCE TO RELATED APPLICATIONS

The present application is a continuation of U.S. patent application Ser. No. 13/186,187, filed on Jul. 19, 2011, entitled "Locking Confirmation Mechanism for a bone Screw and Plate Assembly," the entire contents of which are incorporated by reference in its entirety.

FIELD OF THE INVENTION

The present application generally relates to bone screw and plate assemblies, and in particular, to locking confirmation mechanisms for bone screw and plate assemblies.

BACKGROUND OF THE INVENTION

Bone screw and plate assemblies are commonly used in spinal surgery to assist in stabilizing bone members. Stabilizing bone plates can extend across one or more vertebral bodies and can include one or more holes for receiving bone screws. Once the bone screws are received in the plates, the bone screws are put into a locked configuration. To confirm that the bone screws are received and/or locked in the plates, it is helpful to provide a surgeon with some kind of visual, audible or tactile feedback.

Thus, there remains a need for improved confirmation mechanisms for confirming that a bone screw is properly locked in a plate.

SUMMARY OF THE INVENTION

The present application relates to novel bone screw and plate assemblies having locking confirmation mechanisms. In some embodiments, a spinal assembly comprises a bone screw having a head portion and a threaded shaft; a plate having an aperture for receiving the bone screw, wherein the bone screw is configured to be in an unlocked configuration and a locked configuration within the plate; and a locking mechanism operatively attached to the plate, wherein the locking confirmation mechanism comprises a toggling arm having an upper portion, a mid-portion and a lower portion, wherein the locking confirmation mechanism is configured to pivot about an axis when the bone screw moves from the unlocked configuration to the locked configuration thereby providing visual confirmation of the bone screw in the locked configuration.

In some embodiments, a spinal assembly comprises a bone screw having a head portion and a shaft; a plate having an aperture for receiving the bone screw, wherein the bone screw is capable of being in an unlocked configuration and a locked configuration within the plate; and a locking confirmation mechanism operably attached to the plate, wherein the locking confirmation mechanism comprises a pivoting arm having an upper portion, a mid-portion and a lower portion, wherein a section of the upper portion of the locking confirmation mechanism is positioned above an uppermost portion of the plate when the screw is in an unlocked configuration and below an uppermost portion of the plate when the screw is in a locked configuration.

In some embodiments, a spinal assembly comprises a bone screw having a head portion and a shaft; a plate having an aperture for receiving the bone screw, wherein the bone screw is capable of being in an unlocked configuration and a locked configuration within the plate; and a locking confirmation mechanism positioned in a slot formed in the plate, wherein the locking confirmation mechanism is capable of pivoting such that when the bone screw is in an unlocked configuration, the locking confirmation mechanism obstructs a space formed in the slot, and wherein when the bone screw is in a locked configuration, the locking confirmation mechanism pivots thereby exposing the space formed in the slot.

DETAILED DESCRIPTION OF THE ILLUSTRATED EMBODIMENTS

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present application generally relates to bone screw and plate assemblies, and in particular, to locking confirmation mechanisms for bone screw and plate assemblies. The locking confirmation mechanisms described herein provide a reliable and convenient mechanism for a surgeon to determine whether a bone screw is in a locked configuration within a plate. Advantageously, the locking confirmation mechanisms provide multiple ways to determine whether a bone screw is in a locked configuration within a plate. The locking confirmation mechanisms are effective whether a bone screw is placed within a plate straight or at an angle.

Figure 1A:
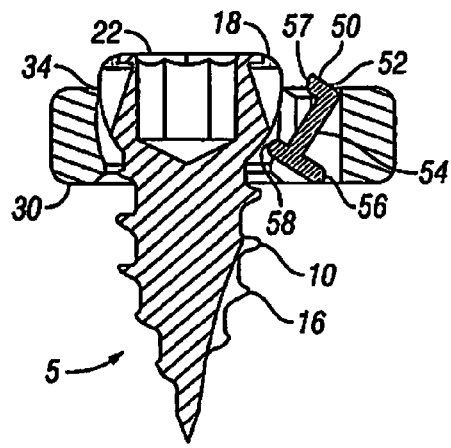
FIG. 1A is a cross-sectional view of a bone screw and plate assembly having a locking confirmation mechanism in an open configuration according to some embodiments.

FIG. 1A is a cross-sectional view of a bone screw and plate assembly having a locking confirmation mechanism in an open configuration according to some embodiments. The bone screw and plate assembly 5 is comprised of a bone screw 10, a plate 30 and a locking confirmation mechanism 50.

The bone screw 10 comprises a threaded shaft 16 that is operatively attached to a head portion 18. The threads of the threaded shaft 16 can extend along the entire length of the threaded shaft, or along only a portion of the entire length of the threaded shaft. In some embodiments, the threads comprise single lead threads, while in other embodiments, the threads comprise dual lead threads.

As shown in the illustrated embodiment, the threaded shaft 16 can have a tapering body. In some embodiments, the threaded shaft 16 assumes the form of a tapering body by having an internal shaft that is tapered, while in other embodiments, the threaded shaft 16 assumes the form of a tapering body by having threads that are of different diameters surrounding an internal shaft that is of a generally constant diameter. In other embodiments, the threaded shaft 16 has a generally constant diameter and is not tapered.

The head portion 18 comprises a generally rounded or cylindrical member that can be seated within the plate 30. The head portion 18 includes a top engagement surface 22 that can receive one or more instruments for driving the bone screw 10 into a bone member. In some embodiments, the head portion 18 is capable of expansion and/or splaying. For example, the head portion 18 can be comprised of a flexible material and/or can include one or more features (e.g., slits) that allow for expansion of the head portion. Such expansion allows the head portion 18 to be securely fixed within a hole or aperture of the plate 30. When the head portion 18 is securely fixed within a hole of the plate 30 (as shown in FIG. 1C), the bone screw 10 is in a locked configuration within the plate 30.

The bone screw 10 can be received in a hole or aperture 34 of a plate 30. While the illustrated embodiment shows a single hole 34, the plate 30 can include multiple holes, including two, three, four, five, six or more. When the bone screw 10 is inserted and placed in a locked configuration within the plate 30, the locking confirmation mechanism 50 can serve as a visual indicator to inform a surgeon that the bone screw 10 is in a locked configuration.

Figure 1B:
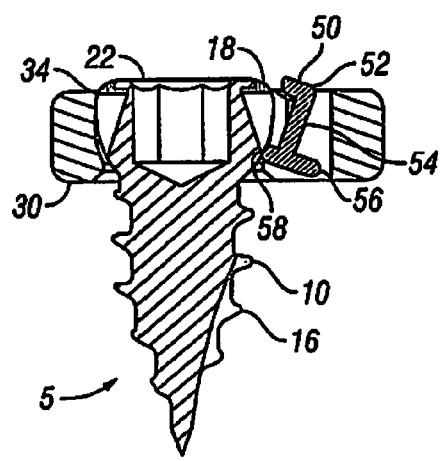
FIG. 1B is a cross-sectional view of the bone screw and plate assembly of FIG. 1A with the locking confirmation mechanism in a partially closed configuration.
Figure 1C:
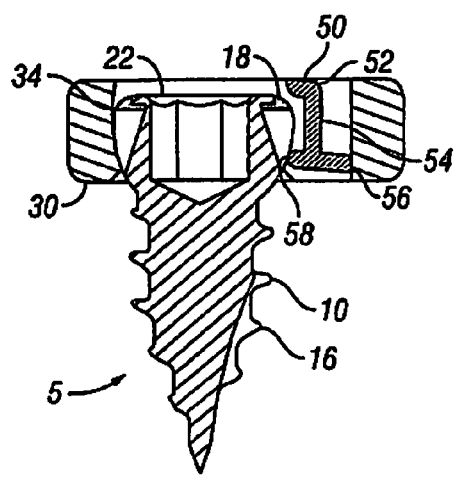
FIG. 1C is a cross-sectional view of the bone screw and plate assembly of FIG. 1A with the locking confirmation mechanism in a closed configuration.

The locking confirmation mechanism 50, shown in different positions in FIGS. 1A-1C, comprises a toggling arm having an upper portion 52, a mid-portion 54 and a lower portion 58 forming a "C" shape. In the illustrated embodiment, the upper portion 52 includes an angulated surface 57 that can accommodate different shaped bone screw heads. In addition, a rear protruding portion 56 extends from the back of the lower portion 58 of the C-shaped section of the locking confirmation mechanism 50. The rear protruding portion 56 advantageously helps the locking confirmation mechanism 50 to be in an orientation that is ready for use, as discussed in further detail below.

As shown in FIGS. 1A-1C, the locking confirmation mechanism 50 is capable of moving, i.e. pivoting or translating about or on an axis from an "open" configuration (FIG. 1A) to a "closed" configuration (FIG. 1C). In the open configuration illustrated in FIG. 1A, the mid-portion 54 of the locking confirmation mechanism 50 is positioned such that a portion of the upper portion 52 of the locking confirmation mechanism 50 is proud and extends above an uppermost surface of the plate 30. As a bone screw 10 is inserted downwardly into a hole 34 of the plate, the bone screw 10 will contact a portion (e.g., the lower portion 58) of the locking confirmation mechanism 50. This contact will begin to move the locking confirmation mechanism 50 into the closed configuration as shown in FIGS. 1B and 1C. The following description of an exemplary operation of the locking confirmation mechanism 50 discusses a pivoting movement of the locking confirmation mechanism 50; however, other means of movement are contemplated including a translating movement and a combination translating and pivoting movement.

As the bone screw 10 is inserted further downwardly through the plate hole 34, thereby moving closer to a locked configuration within the plate 30, the locking confirmation mechanism 50 continues to pivot. As shown in FIG. 1B, which illustrates the locking confirmation mechanism 50 in a partially-closed (or partially-opened) configuration midway between the open and closed configurations, as the bone screw 10 is inserted further downward, the upper portion 52 of the locking confirmation mechanism 50 pivots towards the head 18 of the bone screw. In the partially-closed configuration in FIG. 1B, the locking confirmation mechanism 50 remains proud above the uppermost portion of the plate 30.

By the time the bone screw 10 is fully secured in a locked configuration in the plate 30, as shown in FIG. 1C, the mid-portion 54 of the locking confirmation mechanism 50 is in a substantially upwards or vertical position. When the bone screw is in the locked configuration, the locking confirmation mechanism 50 no longer pivots toward the bone screw. As shown in FIG. 1C, a portion of the upper portion 52 of the locking confirmation mechanism 50 can rest above or higher than the top surface of the bone screw 10. However, in the closed configuration, the upper portion 52 of the locking confirmation mechanism 50 is no longer proud above the uppermost surface of the plate 30 (as shown in FIG. 1C), thereby advantageously providing a low-profile, visual means to assess whether the bone screw 10 is in a locked configuration in the plate 30.

As discussed above, the locking confirmation mechanism 50 includes a rear protruding portion 56. Advantageously, the rear protruding portion 56 helps to ensure that the locking confirmation mechanism 50 is readily available in a position for use. With the rear protruding portion 56, the locking confirmation mechanism 50 will not be overly pivoted in a forward direction (e.g., the upper portion 52 moving in the direction of the midline axis A-A), as the back surface of the rear protruding portion 56 will contact a side wall of the aperture 34 of the plate 30 before any over-pivoting occurs.

Advantageously, the locking confirmation mechanism 50 does not affect how the bone screw 10 locks into the plate 30. In other words, the locking confirmation mechanism 50 simply provides confirmation of when the bone screw 10 is locked in the plate 30, and does not affect the locking operation itself. This advantageously allows the locking confirmation mechanism 50 to work with a variety of different bone screw and plate assemblies having a wide range of designs.

Figure 2:
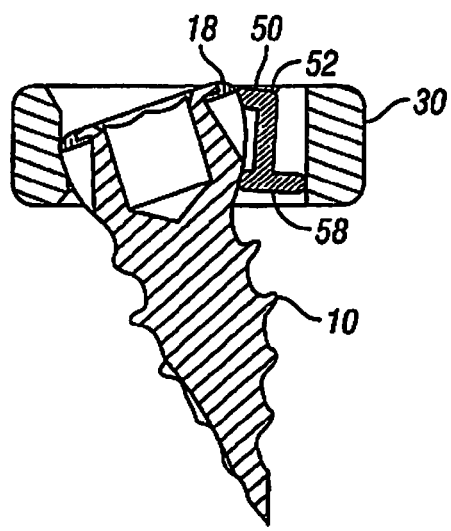
FIG. 2 is a cross-sectional view of a bone screw and plate assembly with the bone screw in an angulated configuration according to some embodiments.

FIG. 2 is a cross-sectional view of a bone screw and plate assembly with the bone screw in an angulated configuration according to some embodiments. As shown in this embodiment, the locking confirmation mechanism 50 works even when the bone screw 10 is angulated into a locked configuration. As the head portion 18 of the angulated bone screw 10 contacts the lower portion 58 of the locking confirmation mechanism 50, the locking confirmation mechanism 50 will pivot from an open to closed position (similar as in FIGS. 1A-1C).

Figure 3A:
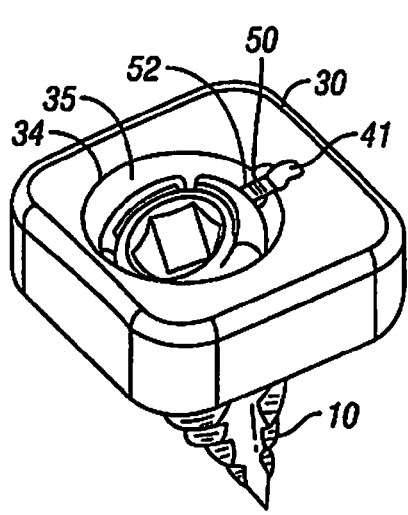
FIG. 3A is a top perspective view of a bone screw and plate assembly with the bone screw in an angulated configuration according to some embodiments.

FIG. 3A is a top perspective view of a bone screw and plate assembly with the bone screw in an angulated configuration according to some embodiments. From this view, it is clearly shown that the locking confirmation mechanism 50 is operable even when the bone screw is angulated through the plate. The upper portion 52 of the locking confirmation mechanism 50 can pivot in between the chamfered area 35 of the plate aperture and toward the head portion of the bone screw 10. The locking confirmation mechanism can move from an open to a closed configuration as shown in FIGS. 1A-1C.

Figure 3B:
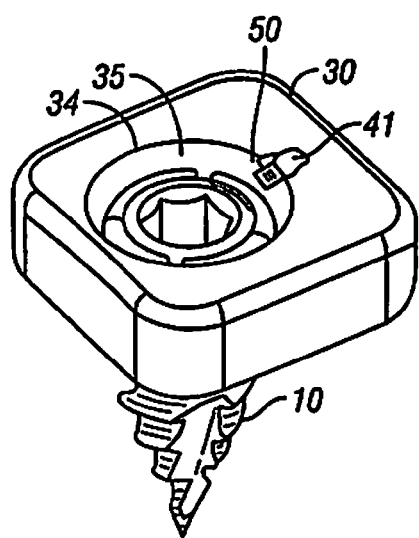
FIG. 3B is a top perspective view of a bone screw and plate assembly with the bone screw in a straight configuration according to some embodiments.

FIG. 3B is a top perspective view of a bone screw and plate assembly with the bone screw in a straight configuration according to some embodiments. The bone screw 10 is shown as having a longitudinal axis that is substantially vertical through the aperture 34 of the plate 30. As in FIG. 3A, this view clearly shows the locking confirmation mechanism 50 operable when the bone screw is straight through the plate.

Figure 4A:
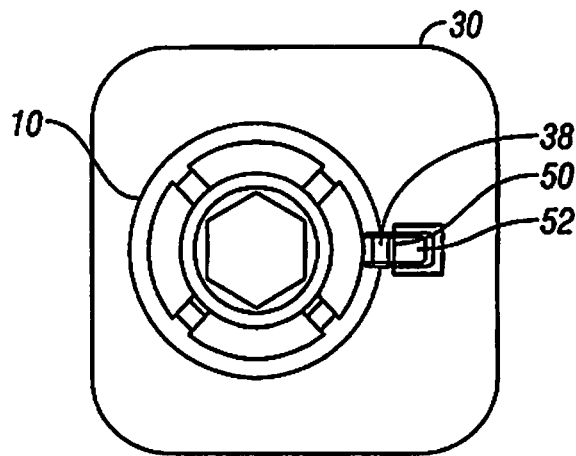
FIG. 4A is a top view of a bone screw and plate assembly with a locking confirmation mechanism in an open configuration according to some embodiments.

FIG. 4A is a top view of a bone screw and plate assembly with a locking confirmation mechanism in an open configuration according to some embodiments. From this view, it is apparent that the locking confirmation mechanism 50 is operably attached and comfortably positioned within an opening or slot 38 formed in the plate 30. In FIG. 4A, the bone screw 10 is not in a locked configuration. Accordingly, the locking confirmation mechanism 50 is not pivoted in the direction of the head portion of the bone screw 10 and therefore stands in an "open" configuration as in FIG. 1A. When the locking confirmation mechanism 50 is an open configuration, the upper portion 52 of the locking confirmation mechanism 50 obstructs a space 60 formed in the slot 38 (shown in FIG. 4B) that is visible when the locking confirmation mechanism 50 is pivoted into a "closed" configuration as in FIG. 1C.

Figure 4B:
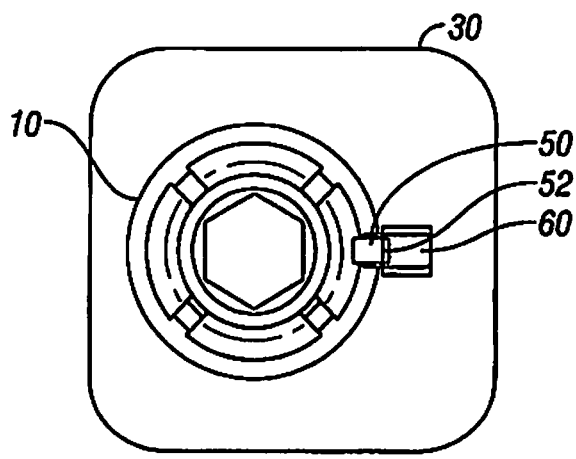
FIG. 4B is a top view of a bone screw and plate assembly with a locking confirmation mechanism in a closed configuration according to some embodiments.

FIG. 4B is a top view of a bone screw and plate assembly with a locking confirmation mechanism in a closed configuration according to some embodiments. In this embodiment, the bone screw 10 stands in a locked configuration such that the locking confirmation mechanism 50 is fully pivoted in the direction of the head portion of the bone screw 10 and therefore stands in a "closed" configuration as in FIG. 1C. When the locking confirmation mechanism 50 is in a pivoted closed configuration, a space 60 is exposed in between the slot 38, thereby advantageously informing a surgeon visually that the bone screw is locked in place within the plate. In addition to providing visual confirmation of locking, a surgeon can also choose to insert an instrument through the space 60 to confirm locking of the bone screw. In this way, the bone screw and plate assembly also advantageously provides a tactile means of providing feedback of locking of the bone screw.

The bone screw and plate assemblies described herein thus include a convenient locking confirmation mechanism that can provide visual and/or tactile feedback to confirm that a bone screw is locked within a plate. The locking confirmation mechanism does not affect how a screw locks into a plate, thereby advantageously accommodating a number of different bone screw and plate assembly designs.

It will be apparent to those skilled in the art that various modifications and variations can be made in the present invention without departing from the scope or spirit of the invention. Moreover, the improved spacer implants and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed spacer implants. Thus, it is intended that the present invention cover the modifications and variations of this invention provided that they come within the scope of the appended claims or their equivalents.

What is claimed is:

1. A surgical method for stabilizing bone members comprising:
   providing a plate having at least one aperture and a locking confirmation mechanism within the plate, wherein the locking confirmation mechanism is capable of pivoting, wherein the locking confirmation mechanism is configured to fit in a slot in the plate;
   inserting a screw down the at least one aperture, wherein the screw includes a head portion and a threaded shaft operatively attached to the head portion,
   wherein as the screw is inserted down the at least one aperture, the screw contacts a lower portion of the locking confirmation mechanism pivoting the locking confirmation mechanism from an open configuration to a closed configuration,
   wherein in the open configuration, an upper portion of the locking confirmation mechanism is located above an uppermost surface of the plate,
   wherein in the closed configuration, the upper portion of the locking confirmation mechanism is located below the uppermost surface of the plate,
   wherein the upper portion of the locking confirmation mechanism is located above the lower portion of the locking confirmation mechanism, and
   wherein the locking confirmation mechanism comprises the upper portion, a mid-portion, and the lower portion separated from the upper portion by the mid-portion, thereby forming a C-shape.

2. The surgical method of claim 1, wherein the at least one aperture comprises two or more apertures.

3. The surgical method of claim 1, wherein the threaded shaft of the screw is threaded only along a portion of the shaft.

4. The surgical method of claim 1, wherein the threaded shaft comprises dual lead threads.

5. The surgical method of claim 1, wherein the locking confirmation mechanism pivots when the screw downwardly pushes on the lower portion of the locking confirmation mechanism.

6. The surgical method of claim 1, wherein in the closed configuration, the upper portion of the locking confirmation mechanism rests above but does not contact the head portion of the screw.

7. The surgical method of claim 1, wherein the threaded shaft of the screw is tapered.

8. A surgical method for stabilizing bone members comprising:
   providing a plate having at least one aperture and a locking confirmation mechanism within the plate, wherein the locking confirmation mechanism is capable of pivoting, wherein the locking confirmation mechanism is configured to fit in a slot in the plate;
   inserting a screw down the at least one aperture, wherein the screw includes a head portion and a threaded shaft operatively attached to the head portion, wherein the threaded shaft comprises a generally constant diameter, wherein as the screw is inserted down the at least one aperture, the screw contacts a lower portion of the locking confirmation mechanism pivoting the locking confirmation mechanism from an open configuration to a closed configuration, wherein in the open configuration, an upper portion of the locking confirmation mechanism is located above an uppermost surface of the plate, wherein in the closed configuration, the upper portion of the locking confirmation mechanism is below the uppermost surface of the plate, and wherein the upper portion of the locking confirmation mechanism is located above the lower portion of the locking confirmation mechanism, and wherein the locking confirmation mechanism comprises the upper portion, a mid-portion, and the lower portion separated from the upper portion by the mid-portion, thereby forming a C-shape.

9. The surgical method of claim 8, wherein the at least one aperture comprises three or more apertures.

10. The surgical method of claim 8, wherein the threaded shaft of the screw is completely threaded along a length of the shaft.

11. The surgical method of claim 8, wherein the threaded shaft comprises single lead threads.

12. The surgical method of claim 8, wherein the head portion of the screw is capable of splaying.

13. The surgical method of claim 8, wherein the locking confirmation mechanism pivots when the screw downwardly pushes on the lower portion of the locking confirmation mechanism.

14. The surgical method of claim 8, wherein in the closed configuration, the upper portion of the locking confirmation mechanism rests above but does not contact the head portion of the screw.

15. A surgical method for stabilizing bone members comprising:

providing a plate having at least one aperture and a locking confirmation mechanism within the plate, wherein the locking confirmation mechanism is capable of pivoting, wherein the locking confirmation mechanism is configured to fit in a slot in the plate;

inserting a screw down the at least one aperture, wherein the screw includes a head portion and a threaded shaft operatively attached to the head portion, wherein the threaded shaft comprises a tapered shaft with dual lead threads, wherein as the screw is inserted down the at least one aperture, the screw contacts a lower portion of the locking confirmation mechanism pivoting the locking confirmation mechanism from an open configuration to a closed configuration, wherein in the open configuration, an upper portion of the locking confirmation mechanism is located above an uppermost surface of the plate, wherein in the closed configuration, the upper portion of the locking confirmation mechanism is below the uppermost surface of the plate, and wherein the upper portion of the locking confirmation mechanism is located above the lower portion of the locking confirmation mechanism, and wherein the locking confirmation mechanism comprises the upper portion, a mid-portion, and the lower portion separated from the upper portion by the mid-portion, thereby forming a C-shape.

16. The surgical method of claim 15, wherein the head portion of the screw is capable of expansion.

17. The surgical method of claim 15, wherein in the closed configuration, the upper portion of the locking confirmation mechanism rests above the head portion of the screw.

18. The surgical method of claim 17, wherein in the closed configuration, the upper portion of the locking confirmation mechanism does not contact the head portion of the screw.

\* \* \* \* \*